US010638919B2

(12) United States Patent
Kinoshita

(10) Patent No.: US 10,638,919 B2
(45) Date of Patent: May 5, 2020

(54) ENDOSCOPE

(71) Applicant: OLYMPUS CORPORATION, Hachioji-shi, Tokyo (JP)

(72) Inventor: Hiroaki Kinoshita, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 352 days.

(21) Appl. No.: 15/831,929

(22) Filed: Dec. 5, 2017

(65) Prior Publication Data

US 2018/0092510 A1 Apr. 5, 2018

Related U.S. Application Data

(63) Continuation of application No. PCT/JP2016/070227, filed on Jul. 8, 2016.

(30) Foreign Application Priority Data

Aug. 3, 2015 (JP) ................................ 2015-153401

(51) Int. Cl.

*A61B 1/00* (2006.01)
*A61B 1/005* (2006.01)
*A61B 1/05* (2006.01)
*G02B 23/24* (2006.01)
*A61B 1/07* (2006.01)

(Continued)

(52) U.S. Cl.

CPC ............ *A61B 1/005* (2013.01); *A61B 1/0011* (2013.01); *A61B 1/0055* (2013.01); *A61B 1/00071* (2013.01); *A61B 1/00142* (2013.01); *A61B 1/00181* (2013.01); *A61B 1/00188* (2013.01); *A61B 1/04* (2013.01); *A61B 1/051* (2013.01); *A61B 1/07* (2013.01); *G02B 23/2423* (2013.01); *A61B 1/015* (2013.01); *A61B 1/018* (2013.01);

(Continued)

(58) Field of Classification Search

None

See application file for complete search history.

(56) References Cited

U.S. PATENT DOCUMENTS 4,753,222 A * 6/1988 Morishita ............ A61B 1/0055 600/140

2002/0010386 A1* 1/2002 Matsushita ........ A61B 1/00071 600/140

(Continued)

FOREIGN PATENT DOCUMENTS

CN 102204806 A 10/2011
EP 2371266 A1 10/2011

(Continued)

OTHER PUBLICATIONS

International Search Report (ISR) and Written Opinion dated Sep. 20, 2016 issued in International Application No. PCT/JP2016/070227.

*Primary Examiner* — Timothy J Neal

(74) *Attorney, Agent, or Firm* — Holtz, Holtz & Volek PC

(57) ABSTRACT

An endoscope includes a flexible portion, a surface of which is covered by an outer covering, the outer covering including a resin layer as an outermost layer and a laminated barrier film that is arranged on an inner side of the resin layer, and the laminated barrier film including a first barrier layer made from a metal oxide, and a second barrier layer made from a metal that is arranged on an inner side of the first barrier layer.

10 Claims, 3 Drawing Sheets

(51) Int. Cl.

| | |
|---|---|
| ***A61B 1/04*** | (2006.01) |
| *A61B 1/018* | (2006.01) |
| *A61B 1/015* | (2006.01) |
| *A61B 90/70* | (2016.01) |
| *A61B 1/06* | (2006.01) |
| *A61B 1/12* | (2006.01) |

(52) U.S. Cl.
CPC ............. *A61B 1/0661* (2013.01); *A61B 1/121* (2013.01); *A61B 2090/701* (2016.02)

(56) References Cited

U.S. PATENT DOCUMENTS

| | | | | |
|---|---|---|---|---|
| 2003/0125679 | A1* | 7/2003 | Kubota | A61L 29/106 604/265 |
| 2005/0043715 | A1* | 2/2005 | Nestenborg | A61M 25/002 604/544 |
| 2011/0245612 | A1 | 10/2011 | Nakamura | |
| 2013/0153446 | A1* | 6/2013 | Utas | A61M 25/002 206/210 |
| 2015/0305596 | A1* | 10/2015 | Oskin | A61B 1/00064 600/104 |
| 2015/0335856 | A1* | 11/2015 | Utas | A61M 25/002 206/210 |

FOREIGN PATENT DOCUMENTS

| | | | |
|---|---|---|---|
| JP | 2003000532 | A | 1/2003 |
| JP | 2005287774 | A | 10/2005 |
| JP | 2006061205 | A | 3/2006 |
| JP | 2007050117 | A | 3/2007 |
| JP | 2011212338 | A | 10/2011 |

* cited by examiner

ENDOSCOPE

CROSS REFERENCE TO RELATED APPLICATION

This application is a continuation application of PCT/JP2016/070227 filed on Jul. 8, 2016 and claims benefit of Japanese Application No. 2015-153401 filed in Japan on Aug. 3, 2015, the entire contents of which are incorporated herein by this reference.

BACKGROUND OF THE INVENTION

1. Field of the Invention

Embodiments of the present invention relate to a flexible endoscope on which a cleaning, disinfecting and sterilization process is performed.

2. Description of the Related Art

An endoscope acquires an image of a subject with an image pickup device through an image pickup optical system that is arranged in a distal end portion of an insertion portion. The image pickup optical system has a plurality of lenses, and spaces among some of the lenses serve as optical path spaces.

A flexible endoscope for medical use (hereunder, referred to as "endoscope") is used to observe an inside of a body cavity by inserting an elongated insertion portion of the endoscope into the body cavity, and the endoscope also performs various kinds of therapy and treatment using a treatment instrument that is inserted into a treatment instrument channel that passes through the insertion portion. When an endoscope that has been used is to be reused for another patient, a cleaning, disinfecting and sterilization process (hereunder, referred to as "sterilization process") is performed on the endoscope after being used, to thereby prevent infection from occurring between a doctor or a nurse and patients via the endoscope.

An immersion process using a disinfectant solution is widely performed as a sterilization process, since processing is possible using a simple apparatus.

In recent years, an autoclave method that sterilizes using high-temperature and high-pressure steam has also come into widespread use. According to the autoclave method, reliability of a sterilization effect is high, no residual toxicity exists, and a running cost is inexpensive.

In a low-temperature plasma sterilization process, damage to resin is less than in the autoclave method. According to the plasma sterilization process, an aqueous hydrogen peroxide solution is evaporated and injected into a sterilization chamber, and thereafter a high frequency is applied inside the sterilization chamber to cause the hydrogen peroxide vapor to enter a plasma state and act on microorganisms.

In Japanese Patent Application Laid-Open Publication No. 2007-050117, a barrier layer that prevents entry of vapor into an inside of a flexible tube for an endoscope is disclosed. It is disclosed that aluminum, alumina, silica, titanium oxide, magnesium fluoride, gold, silver, platinum, tantalum oxide, niobium oxide or silicon nitride is used for a barrier layer that is arranged between a first resin layer and a second resin layer of an outer covering that covers a surface of the flexible tube.

SUMMARY OF THE INVENTION

An endoscope of an embodiment of the present invention includes: an insertion portion having: a distal end portion in which an image pickup unit having an image pickup optical system including a plurality of lenses is arranged, a bending portion configured to change a direction of the distal end portion that is provided in an extending manner from the distal end portion, and a flexible portion that is provided in an extending manner from the bending portion; and an operation portion that is arranged at a proximal end portion of the insertion portion; wherein: a surface of the flexible portion is covered by an outer covering; the outer covering has a resin layer as an outermost layer, and a laminated barrier film that is arranged on an inner side of the resin layer; and the laminated barrier film includes a first barrier layer made from a metal oxide, and a second barrier layer that is made from a metal and that is arranged on an inner side of the first barrier layer.

DETAILED DESCRIPTION OF THE PREFERRED EMBODIMENT(S)

First Embodiment

An endoscope 10 of a first embodiment of the present invention will be described using FIG. 1 to FIG. 4.

It should be noted that, in the following description, drawings are schematic ones in which a relationship between a thickness and a width of each portion, thickness ratios of the respective portions and the like are different from a relationship and ratios of actual portions, and the drawings may include portions in which dimensional relationships and ratios are different from one another. Further, diagrammatic representation of some constituent elements is omitted in some cases.

Figure 1:
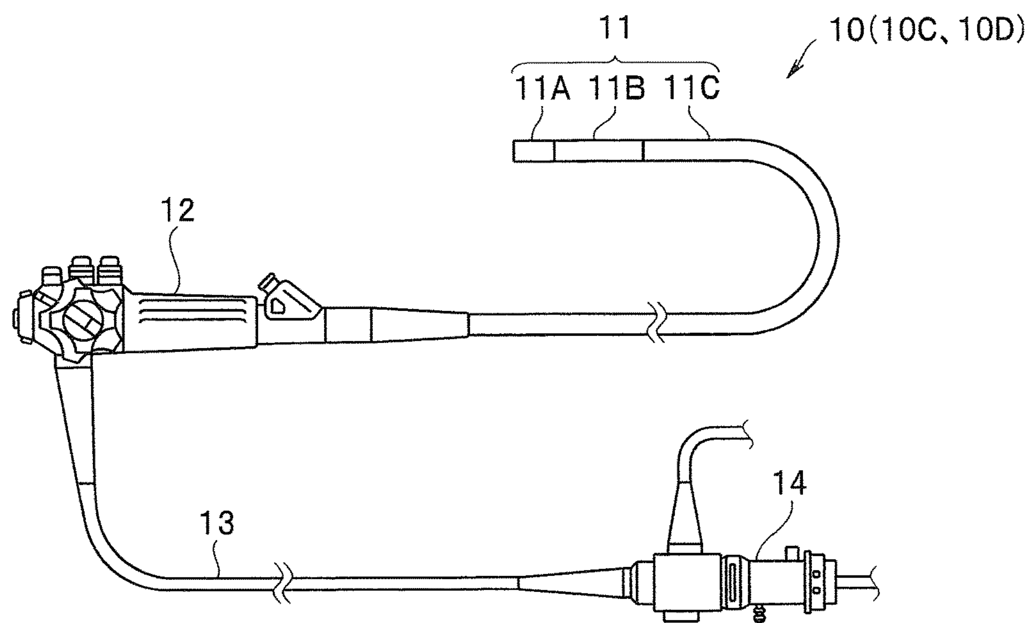
FIG. 1 is a perspective view of an endoscope according to an embodiment.

As illustrated in FIG. 1, an endoscope 10 includes an insertion portion 11 having a length of 3.5 meters, an operation portion 12 that is arranged on a proximal end side of the insertion portion 11, a universal cord 13 provided in an extending manner from the operation portion 12, and a connector 14 arranged on a proximal end side of the universal cord 13. Although not illustrated in the drawings, the connector 14 is connected to a light source apparatus configured to generate illuminating light, a processor configured to process image signals, and an air/water feeding apparatus.

The insertion portion 11 includes a rigid distal end portion 11A in which an image pickup unit 20 is arranged, a bending portion 11B configured to change a direction of the distal end portion 11A and provided in an extending manner from the distal end portion 11A, and an elongated flexible portion 11C with flexibility which is arranged on a proximal end side of the bending portion 11B. The bending portion 11B bends by an operation of a surgeon via bending operation wires 31 (see FIG. 4) that are provided in an extending manner as far as the operation portion 12.

Figure 2:
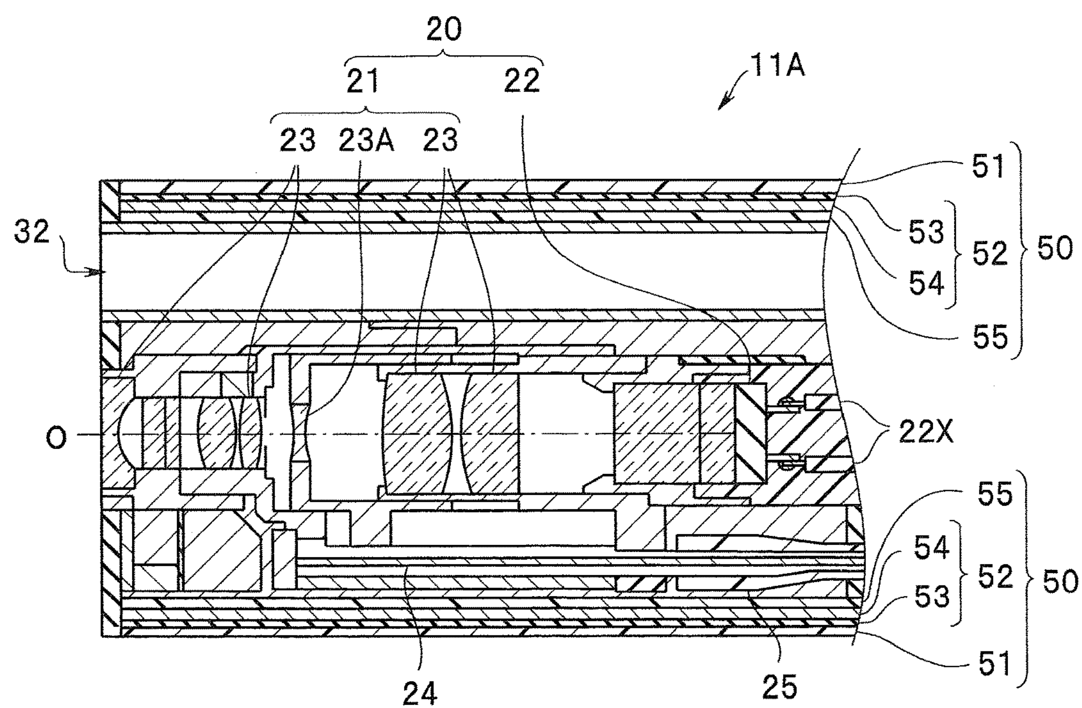
FIG. 2 is a cross-sectional view along a longitudinal direction of a distal end portion of an endoscope of a first embodiment.

As illustrated in FIG. 2, the image pickup unit 20 that includes an image pickup optical system 21 including a plurality of lenses 23, and an image pickup device 22 configured to acquire an object image through the image pickup optical system 21 is arranged in the distal end portion 11A. The respective outer faces of several lenses 23 of the image pickup optical system 21 come into contact with an optical path space (internal space of the image pickup optical system 21). Consequently, if vapor penetrates into the internal space of the image pickup optical system 21, there is a risk that the vapor will cause fogging of the lenses 23. Signal cables 22X that are bonded to the image pickup device 22 are connected to a processor (not illustrated in the drawings) through the connector 14.

The image pickup unit 20 is constituted by a plurality of members including the image pickup optical system 21 and the image pickup device 22. The image pickup optical system 21 is also constituted by a plurality of members. The aforementioned plurality of members are bonded using a resin such as an epoxy resin or a silicone resin. In other words, spaces among the plurality of members, that is, the internal spaces of the image pickup optical system 21, are sealed with a resin and not with a metal such as a solder.

The image pickup optical system 21 is a zoom optical system in which a lens 23A is movable in an optical axis (0) direction. The lens 23A is caused to move forward and rearward in an optical axis direction by an operation of the surgeon through a lens operation wire 24 that is provided in an extending manner up to the operation portion 12. The lens operation wire 24, for example, is housed inside a sheath pipe 25 made from resin that passes through the bending portion 11B and the flexible portion 11C.

A forceps tube 32, an air/water feeding tube 33 (see FIG. 4) and a light guide 34 (see FIG. 4) which pass through the bending portion 11B and the flexible portion 11C are also arranged in the distal end portion 11A.

The distal end portion 11A has a frame body (not illustrated in the drawings), a surface of which is covered by an outer covering 50.

Figure 3:
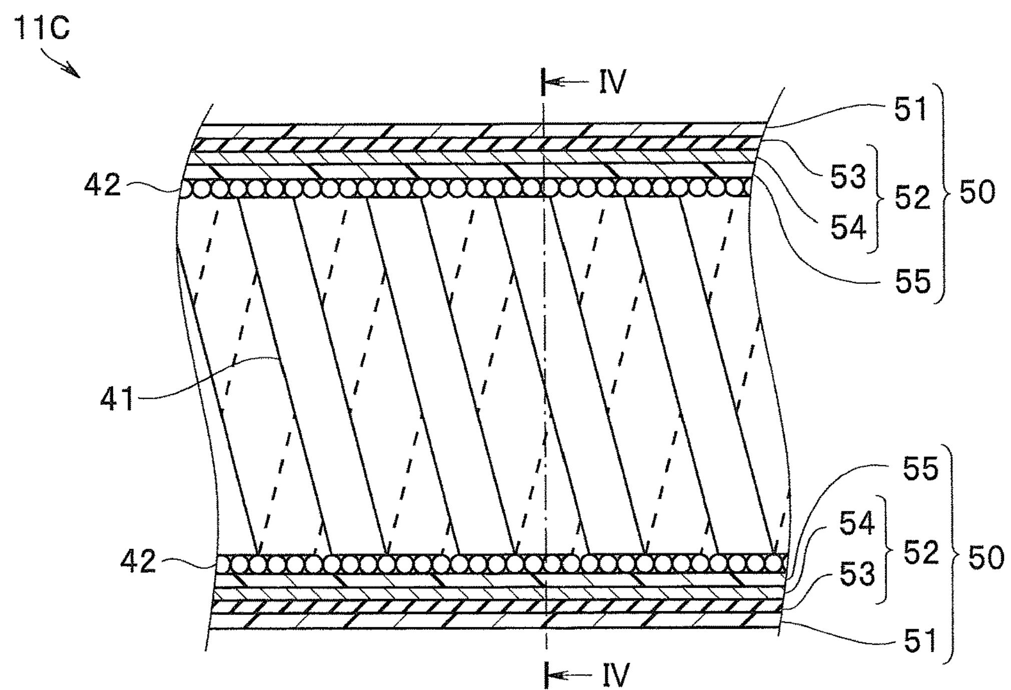
FIG. 3 is a cross-sectional view along a longitudinal direction of a flexible portion of the endoscope of the first embodiment.
Figure 4:
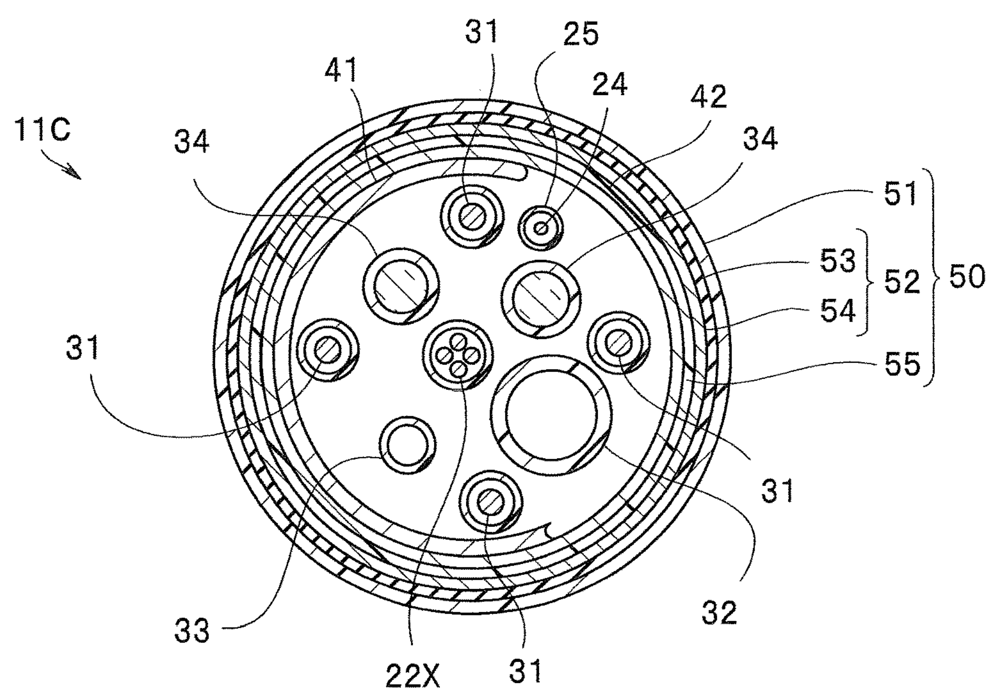
FIG. 4 is a cross-sectional view along an orthogonal direction of the flexible portion of the endoscope of the first embodiment.

On the other hand, as illustrated in FIG. 3 and FIG. 4, the flexible portion 11C includes: a helical tube 41 through which the forceps tube 32 and the like are inserted and which is formed by winding an elastic belt-shaped thin plate material in a spiral shape from an inner peripheral surface side; a mesh tube 42 that is disposed so as to cover the helical tube 41 and is faulted by, for example, weaving stainless steel wire into a tube shape; and the outer covering 50 that is disposed so as to cover the mesh tube 42. Note that, the forceps tube 32 and the like that are inserted through the inside of the helical tube 41 are not illustrated in FIG. 3.

Note that, apart from being a helical tube formed by spirally winding one piece of an elastic belt-shaped thin plate material as illustrated in FIG. 3, the helical tube 41 may be a helical tube formed using two pieces of an elastic belt-shaped thin plate material that are spirally wound in different directions and superimposed on each other, or may be a helical tube formed by spirally winding three pieces of an elastic belt-shaped thin plate material in respectively different directions and superimposing the three pieces of an elastic belt-shaped thin plate material on each other or the like.

The surface of the flexible portion 11C is also covered with the outer covering 50 of the same structure as in the case of the distal end portion 11A. Further, although not illustrated in the drawings, the surface of the bending portion 11B is also covered with the outer covering 50. That is, the surface other than a distal end face of the insertion portion 11 of the endoscope 10 is covered with the outer covering 50.

After an examination and treatment is completed, the endoscope 10 is subjected to a low-temperature plasma sterilization process. As already described above, in the low-temperature plasma sterilization process an aqueous hydrogen peroxide solution is evaporated and injected into a sterilization chamber, and thereafter a high frequency is applied inside the sterilization chamber to turn the hydrogen peroxide vapor into a plasma state to act on microorganisms.

For example, according to a Sterrad® NX process, a 58% hydrogen peroxide solution is used as a precursor, and processing is performed for approximately 38 minutes inside a sterilization chamber in which an endoscope is housed. The processing temperature is a comparatively low temperature of around 50° C.

Although the low-temperature plasma sterilization process is a process in which damage to the endoscope is minor in comparison to the autoclave process and the like, if the process is repeatedly performed due to use of the endoscope over a long period of time, the risk that fogging of the lenses 23 will occur exists.

The main cause for fogging of the lenses 23 has conventionally been considered to be the penetration of vapor from the outer face (front face) of the distal end portion 11A. Therefore, emphasis has been placed on sealing the image pickup unit 20. In contrast, the inventor considered that the likely cause of fogging of the lenses 23 is that moisture penetrated through the outer covering which had been damaged by sterilization processing, particularly, through the outer covering that covers the flexible portion 11C which has a wide surface area, and arrived as far as the distal end portion 11A.

The inventor experimentally produced a plurality of endoscopes (embodiments/comparative examples) in which the configurations of the respective outer coverings were different to each other, and performed the Sterrad® NX process 800 times on each of the endoscopes. After the processes were performed, a high-temperature and high-humidity test was performed to check for the presence or absence of the occurrence of fogging of a lens.

The high-temperature and high-humidity test is a test in which 70 cm at the distal end of the insertion portion of the endoscope is left to stand for 48 hours inside a high-temperature and high-humidity chamber at a temperature of 85° C. and a humidity of 85%, and thereafter the distal end portion is immediately immersed for one minute in water at a temperature of 20° C. to cool, and the presence or absence of the occurrence of fogging of a lens is then confirmed based on an endoscopic image.

In the endoscope 10 of the present embodiment, the outer covering 50 includes a resin layer 51 as an outermost layer, a laminated barrier film (hereunder, referred to as "barrier film") 52 that is arranged inside the resin layer 51, and a base resin layer 55. In the barrier film 52 of the endoscope 10 of the embodiment, a first barrier layer 53 made from tin oxide and a second barrier layer 54 made from metallic tin are laminated together.

That is, as illustrated in FIG. 2 to FIG. 4, the outer covering 50 includes the resin layer 51 that is made from urethane resin of a thickness of 50 μm as an outermost layer, and the barrier film 52 that is arranged on the inner side of the resin layer 51. In the barrier film 52, the first barrier layer 53 having a thickness of 500 nm that is made from aluminum oxide, and the second barrier layer 54 having a thickness of 1 μm that is made from metallic aluminum are laminated together. Note that, the metallic aluminum is deposited on the base resin layer (urethane resin tube) 55 having a thickness of 3 μm. The resin layer (first resin layer) 51 that is the outermost layer and the base resin layer (second resin layer) 55 may be constituted by polyester, nylon, rubber or a resin such as silicone as long as the relevant material is flexible, and the resin layer 51 and the base resin layer 55 may be constituted by different resins to each other.

In the barrier film 52, the first barrier layer 53 made from metal oxide that is on the outer side (outer face side) prevents corrosion by chemicals, and the second barrier layer 54 made from metal that is on the inner side prevents the penetration of vapor.

In the case of the endoscope 10, the lenses 23 did not fog up even in the high-temperature and high-humidity test performed after the low-temperature plasma sterilization process was carried out 800 times. Further, although the endoscope 10 has the image pickup optical system 21 that has a zoom function, fogging up of the lenses 23 did not occur. In addition, although in the endoscope 10 the plurality of members of the image pickup unit 20 were sealed with resin and not metal, fogging up of the lenses 23 did not occur.

That is, in the case of the endoscope 10, because it is difficult for the humidity inside the flexible portion 11C to increase even if a sterilization process is performed, there is no risk of the lenses 23 of the image pickup optical system 21 fogging up.

Comparative Example 1

Although an endoscope 10A (not illustrated in the drawings) of Comparative Example 1 had approximately the same configuration as the endoscope 10, the outer covering of the endoscope 10A did not include a barrier layer and was constituted by only a urethane resin tube having a thickness of 50 μm. The internal space of the image pickup unit was sealed with a resin. In the case of the endoscope 10A, fogging of lenses was observed in a high load test (high-temperature and high-humidity test).

Note that, in the case of the endoscope 10A, after being allowed to stand inside a high-temperature and high-humidity chamber, the humidity became 95% in a short time according to a hygrometer that was inserted inside the insertion portion.

That is, it is considered that vapor that penetrated into the insertion portion reached the distal end portion in which the image pickup optical system 21 was arranged through the forceps tube 32, the air/water feeding tube 33 and the sheath pipe 25 that were inserted through the insertion portion as far as the distal end portion, and caused lenses to fog up.

Note that, even when the outer covering was constituted only by urethane resin similarly to the endoscope 10A, the lenses of the endoscope in which the plurality of members of the image pickup unit were sealed with metal were less liable to become fogged up in comparison to the endoscope 10A. However, the work for sealing the image pickup unit with metal is complicated, and the image pickup unit cannot be easily disassembled when repairs are required.

Further, particularly in the endoscope in which the image pickup optical system having a zoom function was arranged in the distal end portion, the lenses fogged up in many cases. It is considered that the reason is that the sheath pipe 25 through which the lens operation wires 24 are inserted is inserted through the image pickup optical system, and hence it is easy for vapor to reach the image pickup optical system through the sheath pipe 25.

Comparative Example 2

In an endoscope 10B (not illustrated in the drawings) as Comparative Example 2, the outer covering had a metal barrier layer that is a single layer on the inner side of the resin layer as the outermost layer. Specifically, the insertion portion was covered with a tube (base resin layer) with a thickness of 3 μm made from polyurethane, a metallic aluminum layer (barrier film) with a thickness of 1 μm was deposited on the surface of the base resin layer, and the metallic aluminum layer was covered with a urethane layer (resin layer) having a thickness of 50 μm.

The endoscope 10B was subjected to a low-temperature plasma sterilization process 800 times, and thereafter a high-temperature and high-humidity test was performed. The results of the high-temperature and high-humidity test showed that fogging of lenses occurred.

Comparative Example 3

In an endoscope 10C (not illustrated in the drawings) as Comparative Example 3, the outer covering had a single barrier layer made from metal oxide on the inner side of a resin layer as an outermost layer. Specifically, an aluminum oxide layer having a thickness of 500 nm was deposited on a urethane tube having a thickness of 3 μm, and the resin layer as the outermost layer was arranged on the aluminum oxide layer. The endoscope 10C was also subjected to a low-temperature plasma sterilization process 800 times, and thereafter a high-temperature and high-humidity test was performed. The results of the high-temperature and high-humidity test showed that fogging of lenses occurred.

Modifications of First Embodiment

In an endoscope 10C of Modification 1, an outer covering 50 includes a resin layer 51 as an outermost layer, a barrier film 52 arranged on the inner side of the resin layer 51, and a base resin layer 55 having a thickness of 2 μm. In the barrier film 52, a first barrier layer 53 having a thickness of 100 nm made from tin oxide and a second barrier layer 54 having a thickness of 4 μm made from metallic tin are laminated together.

In an endoscope 10D of Modification 2, an outer covering 50 includes a resin layer 51 as an outermost layer, a barrier film 52 arranged on the inner side of the resin layer 51, and a base resin layer 55 having a thickness of 3 μm that is arranged on the inner side of the barrier film 52. In the barrier film 52, a first barrier layer 53 having a thickness of 30 nm made from an oxide of an alloy of titanium and tin (50 at % Ti-50 at % Sn), and a second barrier layer 54 having a thickness of 700 nm made from an alloy of titanium and tin (50 at % Ti-50 at % Sn) are laminated together.

In the endoscope 10C and endoscope 10D, lenses did not fog up even when a high-temperature and high-humidity test was performed after conducting a low-temperature plasma sterilization process 800 times.

Further, as a result of further producing endoscopes of various kinds of configurations, it was found that the following configurations are preferable because of no risk of lenses fogging up even in a high-temperature and high-humidity test.

It is preferable from the viewpoint of vapor barrier properties and chemical resistance that one or more elements selected from Sn, Al, Ti, Zn, Si, V, Cr, Fe, Co, Ni, Cu, Zn, Zr, Nb, In, Hf, Y, Ta, W, Re, Os, Ir, Pt, Au, Bi, La, Gd and Lu is adopted for the metal and the metal oxide, respectively, of the barrier film 52. Furthermore, it is particularly preferable that one or more elements selected from Sn, Al, Ti and Zn is adopted as a principal component of the metal and the metal oxide, respectively, of the barrier film 52, since the aforementioned elements Sn, Al, Ti and Zn are inexpensive and excellent in flexibility. Note that, the term "principal component" means the component for which the content (mass %) is highest.

Note that, as long as the thickness of the barrier film 52 is within a range of 40 nm to 10 μm and the thicknesses of the first barrier layer 53 and the second barrier layer 54 are each within a range of 20 nm to 5 μm, vapor barrier properties and chemical resistance can be guaranteed and it is difficult for interfacial peeling (delamination) to occur.

More preferably, the thickness of the barrier film 52 is within a range of 60 nm to 2 μm and the thicknesses of the first barrier layer 53 and the second barrier layer 54 are each within a range of 30 nm to 1 μm.

Note that, the thickness of the first barrier layer 53 is preferably within a range of 1/50 to 1/2 of the thickness of the second barrier layer 54.

In some cases, a natural oxide layer is formed on the surface of the second barrier layer 54 that is made from metal. However, the natural oxide layer is less than 10 nm, and unlike the first barrier layer 53 of 10 nm or more that is actively deposited, the natural oxide layer cannot guarantee adequate chemical resistance.

Further, because the bending portion 11B sometimes bends by an extremely large amount, a risk exists that partial interfacial peeling or cracking of the barrier film 52 will occur. However, because the surface area that is the penetration route of vapor of the bending portion 11B is not wide, the influence of the bend is minor. On the other hand, the major part of the surface of the insertion portion 11 that is the main penetration route of vapor is the surface of the flexible portion 11C. Because the flexible portion 11C does not become deformed by an amount that is large to the extent of the deformation of the bending portion 11B, it is difficult for interfacial peeling of the barrier film 52 to occur in comparison to the bending portion 11B.

Note that the barrier film 52 of the outer covering 50 need not necessarily cover the entire surface of the insertion portion 11. For example, as long as the barrier film 52 is arranged on 90% or more of the outer circumferential face of the flexible portion 11C, a predetermined effect can be obtained.

Although a method for arranging the barrier film 52 on the outer circumferential face of the cylindrical insertion portion 11 is not particularly limited, it is preferable to use a known vapor phase film formation method such as CVD that is a plasma method, vapor deposition or sputtering. In particular, a so-called "atmospheric pressure plasma method" in which film formation is performed at a pressure in the vicinity of atmospheric pressure (for example, 90 to 110 kPa) can be particularly preferably used from the viewpoint of cost and uniformity of the film thickness.

In addition, to facilitate manufacturing, preferably the same metal, for example, Sn, Al or Ti is adopted as the principal component of the first barrier layer 53 and the second barrier layer 54. For example, by means of the atmospheric pressure plasma method, the second barrier layer 54 made from metal can be formed to a predetermined thickness in a film forming atmosphere that does not include oxygen, and by thereafter starting the introduction of oxygen, the first barrier layer 53 made of metal oxide can be formed in a continuous manner. It is easy to manufacture the endoscope in which the laminated barrier films (the first barrier layer 53 and the second barrier layer 54) are formed in a continuous manner by the atmospheric pressure plasma method.

Note that, literature regarding determining whether to use the atmospheric pressure plasma method to continuously form the laminated barrier film or to use another method to form the laminated barrier film based on the structure or characteristics of the laminated barrier film could not be found. In addition, analyzing and identifying the structure or characteristics based on measurement is also impossible or impractical. That is, more specifically, even when observation by Auger electron spectroscopy or electron microscope and X-ray analysis was used, a difference between the two could not be found.

Further, in a case where the first barrier layer 53 and the second barrier layer 54 are made from the same metal, by gradually increasing the amount of oxygen that is introduced during film formation, a barrier film 52 in which the composition has a gradient in the thickness direction, that is, a barrier film 52 in which the oxygen content gradually changes can also be formed.

A composition-gradient barrier film is superior in corrosion resistance and vapor barrier properties.

Although the interface between the first barrier layer 53 and the second barrier layer 54 is not clear in the case of a composition-gradient film, the thicknesses of the first barrier layer 53 and the second barrier layer 54 are set by regarding a depth at which the oxygen content becomes 50% of the oxygen content of the first barrier layer 53 as the interface between the two layers.

Second Embodiment

Figure 5:
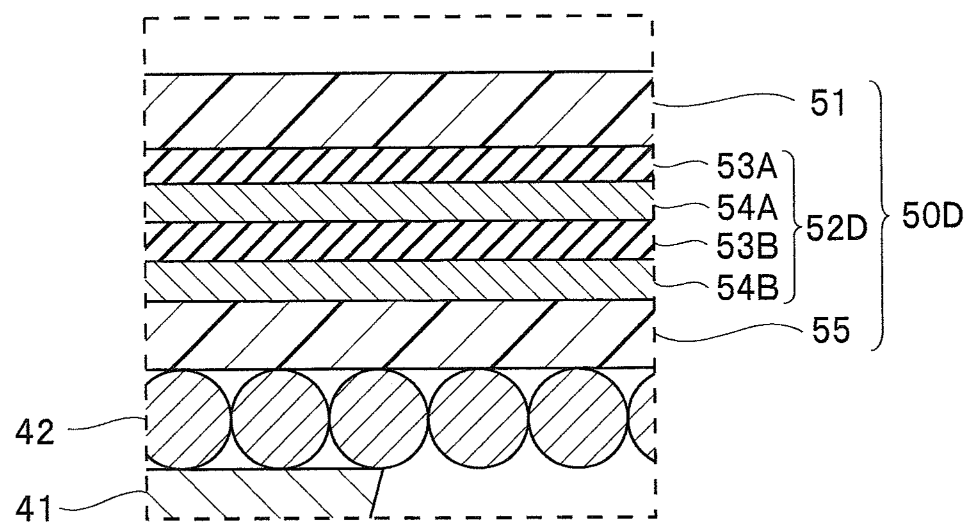
FIG. 5 is a partial cross-sectional view along a longitudinal direction of a flexible portion of an endoscope of a second embodiment.

In the above description, the endoscopes 10, 10C and 10D having the laminated barrier film 52 with a two-layer structure that is made from the first barrier layer 53 and the second barrier layer 54 were described. However, as in the case of an endoscope 10E (not illustrated in the drawings) of the second embodiment that is shown in FIG. 5, a configuration may also be adopted in which a laminated barrier film 52D of an outer covering 50D includes a plurality of first barrier layers 53A and 53B made from metal oxide and a plurality of second barrier layers 54A and 54B made from metal which are laminated together.

In a case where three or more barrier layers are laminated together, it is sufficient that the total thicknesses of the respective barrier layers are the same as the thickness of the monolayer barrier layer. The first barrier layer made from metal oxide lacks ductility in comparison to the second barrier layer that is made from metal. Therefore, if the first barrier layer is formed with a thick thickness in order to adequately guarantee vapor barrier properties and chemical resistance, a risk exists that interfacial peeling or cracking of the first barrier layer will occur due to deformation of the flexible portion 11C.

In an endoscope in which a thick first barrier layer is divided into a plurality of thin barrier layers, and a laminated barrier film that has a second barrier layer among the plurality of thin barrier layers covers the flexible portion 11C, it is difficult for the first barrier layer to undergo interfacial peeling or cracking even if the first barrier layer is deformed.

Note that, although in the above embodiments a so-called flexible endoscope in which the insertion portion has an elongated flexible portion is described, it is clear that the effect of the present invention also applies to a rigid endoscope in which the insertion portion is rigid.

Further, it is clear that, by adopting a similar configuration with respect to an endoscope for industrial use also, the present invention also has an effect in a high-temperature and high-humidity corrosive environment.

As described above, the endoscopes (10; 10C; 10D) of the embodiments include: an insertion portion (11) having a distal end portion (11A) in which an image pickup unit (20) having an image pickup optical system (21) including a plurality of lenses (23) is arranged, a bending portion (11B) provided in an extending manner from the distal end portion (11A) configured to change a direction of the distal end portion (11A), and a flexible portion (11C) provided in an extending manner from the bending portion (11B); and an operation portion (12) arranged at a proximal end portion of the insertion portion (11); wherein: the surface of the flexible portion (11C) is covered by an outer covering (50); the outer covering (50) includes a resin layer (first resin layer: 51) that is an outermost layer, a laminated barrier film (52) arranged on an inner side of the resin layer (51), and a base resin layer (second resin layer: 55) arranged on an inner side of the laminated barrier film (52); and the laminated barrier film (52) includes a first barrier layer (53; 53A, 53B) made from a metal oxide, and a base resin layer (second barrier layer: 54; 54A, 54B) that is made from a metal and is arranged on an inner side of the first barrier layer (53; 53A, 53B).

The present invention is not limited to the above described embodiments and modifications, and various changes and modifications can be made within a range that does not change the gist of the present invention.

What is claimed is:

1. An endoscope, comprising:

an insertion portion including a distal end portion in which an image pickup unit including an image pickup optical system including a plurality of lenses is arranged, a bending portion configured to change a direction of the distal end portion and provided in an extending manner from the distal end portion, and a flexible portion provided in an extending manner from the bending portion; and an operation portion that is arranged at a proximal end side of the insertion portion, wherein:

a surface of the flexible portion is covered with an outer covering, the outer covering includes a resin layer as an outermost layer, and a laminated barrier film that is arranged on an inner side of the resin layer, and the laminated barrier film includes a first barrier layer comprising a metal oxide, and a second barrier layer that comprises a metal and that is arranged on an inner side of the first barrier layer.

2. The endoscope according to claim 1, wherein each of the metal and the metal oxide includes one or more elements selected from Sn, Al, Ti, Zn, Si, V, Cr, Fe, Co, Ni, Cu, Zr, Nb, In, Hf, Y, Ta, W, Re, Os, Ir, Pt, Au, Bi, La, Gd and Lu as a principal component.

3. The endoscope according to claim 2, wherein each of the metal and the metal oxide includes one or more elements selected from Sn, Al, Ti and Zn as a principal component.

4. The endoscope according to claim 3, wherein the first barrier layer and the second barrier layer include the same metal as a principal component.

5. The endoscope according to claim 4, wherein the first barrier layer and the second barrier layer include Sn, Al or Ti as a principal component.

6. The endoscope according to claim 5, wherein the laminated barrier film is a composition-gradient film in which a composition gradually changes from the first barrier layer to the second barrier layer.

7. The endoscope according to claim 1, wherein a thickness of the first barrier layer is within a range of 1/50 to 1/2 of a thickness of the second barrier layer.

8. The endoscope according to claim 1, wherein one or more lenses of the image pickup optical system is movable in an optical axis direction.

9. The endoscope according to claim 1, wherein a space among a plurality of members of the image pickup unit is sealed with a resin.

10. The endoscope according to claim 1, wherein the laminated barrier film is continuously formed by an atmospheric pressure plasma method.

* * * * *